United States Patent
Margallo Balbás et al.

(10) Patent No.: US 10,206,584 B2
(45) Date of Patent: Feb. 19, 2019

(54) OPTICAL COHERENCE TOMOGRAPHY PROBE FOR CROSSING CORONARY OCCLUSIONS

(71) Applicant: Medlumics S.L., Tres Cantos-Madrid (ES)

(72) Inventors: Eduardo Margallo Balbás, Madrid (ES); Alejandro Barriga Rivera, Sevilla (ES); José Luis Rubio Guivernau, Madrid (ES); Santiago Jiménez Valero, Madrid (ES); Juan Lloret Soler, Madrid (ES)

(73) Assignee: MEDLUMICS S.L., Madrid (ES)

( * ) Notice: Subject to any disclaimer, the term of this patent is extended or adjusted under 35 U.S.C. 154(b) by 348 days.

(21) Appl. No.: 14/820,255

(22) Filed: Aug. 6, 2015

(65) Prior Publication Data
US 2016/0038031 A1 Feb. 11, 2016

Related U.S. Application Data

(60) Provisional application No. 62/035,301, filed on Aug. 8, 2014.

(51) Int. Cl.
*A61B 5/00* (2006.01)
*A61B 5/02* (2006.01)
(Continued)

(52) U.S. Cl.
CPC ........ *A61B 5/0084* (2013.01); *A61B 1/00009* (2013.01); *A61B 1/0016* (2013.01);
(Continued)

(58) Field of Classification Search
CPC ..... A61B 17/00; A61B 18/18; A61B 1/00009; A61B 1/00045; A61B 1/00087;
(Continued)

(56) References Cited

U.S. PATENT DOCUMENTS

| 4,669,815 A | * | 6/1987 | Thaniyavarn | G02B 6/126 385/11 |
| 5,336,252 A | * | 8/1994 | Cohen | A61M 25/09 606/129 |

(Continued)

FOREIGN PATENT DOCUMENTS

WO WO 2015/114088 A1 8/2015

OTHER PUBLICATIONS

International Search Report directed to related International Patent Application No. PCT/EP2015/068256, dated Apr. 13, 2016; 6 pages.
(Continued)

*Primary Examiner* — Amanda Hulbert
(74) *Attorney, Agent, or Firm* — Sterne, Kessler, Goldstein & Fox P.L.L.C.

(57) ABSTRACT

Systems and methods for controlling a guide with the aid of optical coherence tomography (OCT) data are described. A guide wire includes at least one optical fiber, a flexible substrate, and one or more optical elements. The at least one optical fiber transmits a source beam of radiation. The flexible substrate includes a plurality of waveguides. At least one of the plurality of waveguides transmits one or more beams of radiation away from the guide wire, and at least one of the plurality of waveguides receives one or more beams of scattered radiation that have been reflected or scattered from a sample. The multiplexer generates the one or more beams of exposure radiation from the source beam of radiation. The one or more optical elements at least one of focus and steer the one or more beams of radiation.

15 Claims, 12 Drawing Sheets

(51) Int. Cl.
*A61M 25/09* (2006.01)
*A61B 1/00* (2006.01)
*A61B 1/07* (2006.01)
*A61B 18/18* (2006.01)
*A61B 17/00* (2006.01)
*A61B 17/22* (2006.01)
*A61B 18/00* (2006.01)

(52) U.S. Cl.
CPC ...... *A61B 1/00045* (2013.01); *A61B 1/00087* (2013.01); *A61B 1/00096* (2013.01); *A61B 1/07* (2013.01); *A61B 5/0066* (2013.01); *A61B 5/02007* (2013.01); *A61B 5/6851* (2013.01); *A61B 5/6852* (2013.01); *A61B 5/6886* (2013.01); *A61B 17/00* (2013.01); *A61B 18/18* (2013.01); *A61M 25/09* (2013.01); *A61B 2017/22038* (2013.01); *A61B 2017/22094* (2013.01); *A61B 2018/0041* (2013.01); *A61B 2018/00982* (2013.01); *A61B 2562/0266* (2013.01); *A61M 2025/09183* (2013.01)

(58) Field of Classification Search
CPC ..... A61B 1/00096; A61B 1/0016; A61B 1/07; A61B 2017/22038; A61B 2017/22094; A61B 2018/0041; A61B 2018/00982; A61B 2562/0266
See application file for complete search history.

(56) References Cited

U.S. PATENT DOCUMENTS

| | | |
|---|---|---|
| 6,175,669 B1 * | 1/2001 | Colston .............. A61B 1/00177 356/511 |
| 6,485,413 B1 | 11/2002 | Boppart et al. |
| 9,062,960 B2 | 6/2015 | Rubio Guivernau et al. |
| 2007/0060847 A1 * | 3/2007 | Leo ...................... A61B 5/0084 600/587 |
| 2007/0139950 A1 * | 6/2007 | Easley .................... A61B 1/07 362/551 |
| 2008/0282741 A1 * | 11/2008 | Shimizu ............. G02B 6/12002 65/386 |
| 2013/0201485 A1 | 8/2013 | Rubio-Guivernau et al. |
| 2014/0078510 A1 | 3/2014 | Rubio-Guivernau et al. |
| 2014/0213893 A1 | 7/2014 | Simpson et al. |
| 2015/0209105 A1 | 7/2015 | Margallo Balbás et al. |

OTHER PUBLICATIONS

Written Opinion of the International Searching Authority directed to related International Patent Application No. PCT/EP2015/068256, dated Apr. 13, 2016; 15 pages.

* cited by examiner

FIG. 4A
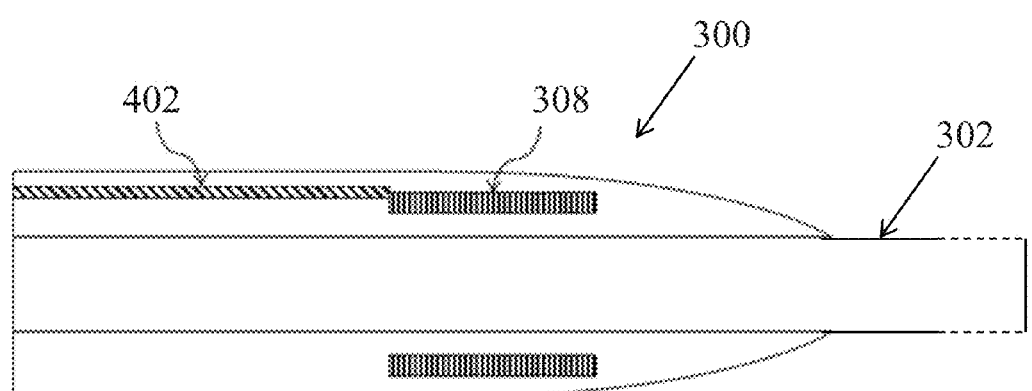
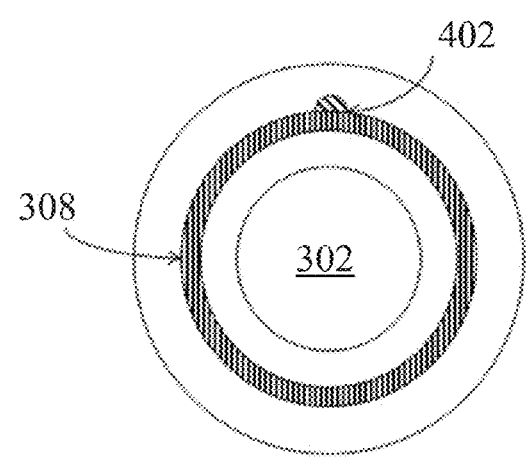
FIG. 4B

OPTICAL COHERENCE TOMOGRAPHY PROBE FOR CROSSING CORONARY OCCLUSIONS

CROSS REFERENCE TO RELATED APPLICATIONS

This application claims the benefit of U.S. Provisional Appl. No. 62/035,301, filed Aug. 8, 2014, the disclosure of which is incorporated by reference herein in its entirety.

BACKGROUND

Field

Embodiments of the invention relate to designs of, and methods of using, a guide wire and/or catheter together with optical tissue inspection.

Background

Coronary artery occlusion refers to the blockage of the blood flow in the coronary artery. Occlusion may be partial or complete and it can cause serious complications: partial occlusion forces the heart to work harder and it may derive into angina whereas complete blockage may cause heart infarction or even death. These occlusions may be produced by a gradual deposition of cholesterol and fatty materials around the wall of the coronary artery.

Partial occlusion may respond to pharmacological treatment (nitrates, calcium antagonists, etc.). In other cases, angioplasty may provide an effective solution for the arterial occlusion. Angioplasty is a percutaneous method that provides a minimally invasive technique to maintain blood flow in blocked arteries. The artery is mechanically widened by means of a balloon catheter. The tip of the catheter is passed across the blockage and then, the balloon is inflated. Afterwards, a stent is usually inserted in the vessel acting as a scaffold at the position of the blockage to maintain blood flow.

Angiography is an x-ray based imaging technique typically used for navigation of the balloon catheter or guide wire through the blood vessels. It is used to visualize blood vessels by means of radio-contrast agents. A less invasive approach is the magnetic resonance angiography, although it requires more complex setups.

Angiography provides only limited information about the occlusion structure and provides very little information about tissue characteristics. Current tools are unable to generate adequate information about the position of the guide-wire regarding the true lumen of the vessel.

BRIEF SUMMARY

In the embodiments presented herein, systems and methods for safely traversing an occlusion using a guide wire or catheter are described.

In an embodiment, a catheter includes a distal section, a proximal section, and a multiplexer. The distal section substantially surrounds a guide wire and includes a plurality of waveguides patterned upon a flexible substrate. At least one of the plurality of waveguides transmits one or more beams of radiation away from the distal section of the catheter, and at least one of the plurality of waveguides receives one or more beams of scattered radiation that have been reflected or scattered from a sample. The distal section also includes one or more optical elements that at least one of focus and steer the one or more beams of radiation. The proximal section includes an optical source that generates a source beam of radiation and a detector that generates depth-resolved optical data associated with the one or more beams of scattered radiation. The multiplexer generates the one or more beams of exposure radiation from the source beam of radiation.

In another embodiment, a guide wire includes at least one optical fiber, a flexible substrate, and one or more optical elements. The at least one optical fiber transmits a source beam of radiation. The flexible substrate includes a plurality of waveguides. At least one of the plurality of waveguides transmits one or more beams of radiation away from the guide wire, and at least one of the plurality of waveguides receives one or more beams of scattered radiation that have been reflected or scattered from a sample. The multiplexer generates the one or more beams of exposure radiation from the source beam of radiation. The one or more optical elements at least one of focus and steer the one or more beams of radiation.

An example method is described. The method includes transmitting one or more beams of radiation via one or more waveguides on a flexible substrate within a guide wire and receiving one or more beams of scattered or reflected radiation from a sample. The method further includes generating, using a processing device, depth-resolved optical data of the sample based on the received one or more beams of scattered or reflected radiation. The method includes determining at least one of a distance between the guide wire and a wall of the artery and a distance between the guide wire and an occlusion within the artery based on the depth-resolved optical data and controlling a position of the guide wire within the artery based on the determined distance or distances.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figure 3:
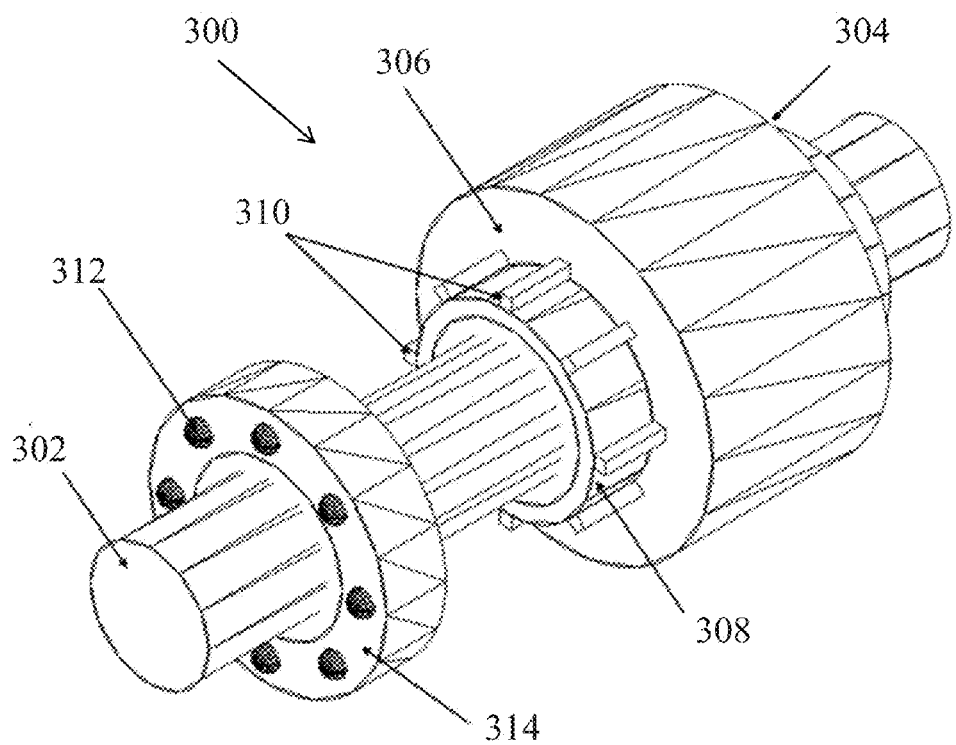

FIG. 3 displays optical elements arranged around a guide wire, according to an embodiment.

FIGS. 4A-4B display optical elements arranged within a catheter, according to embodiments.

Figure 5:
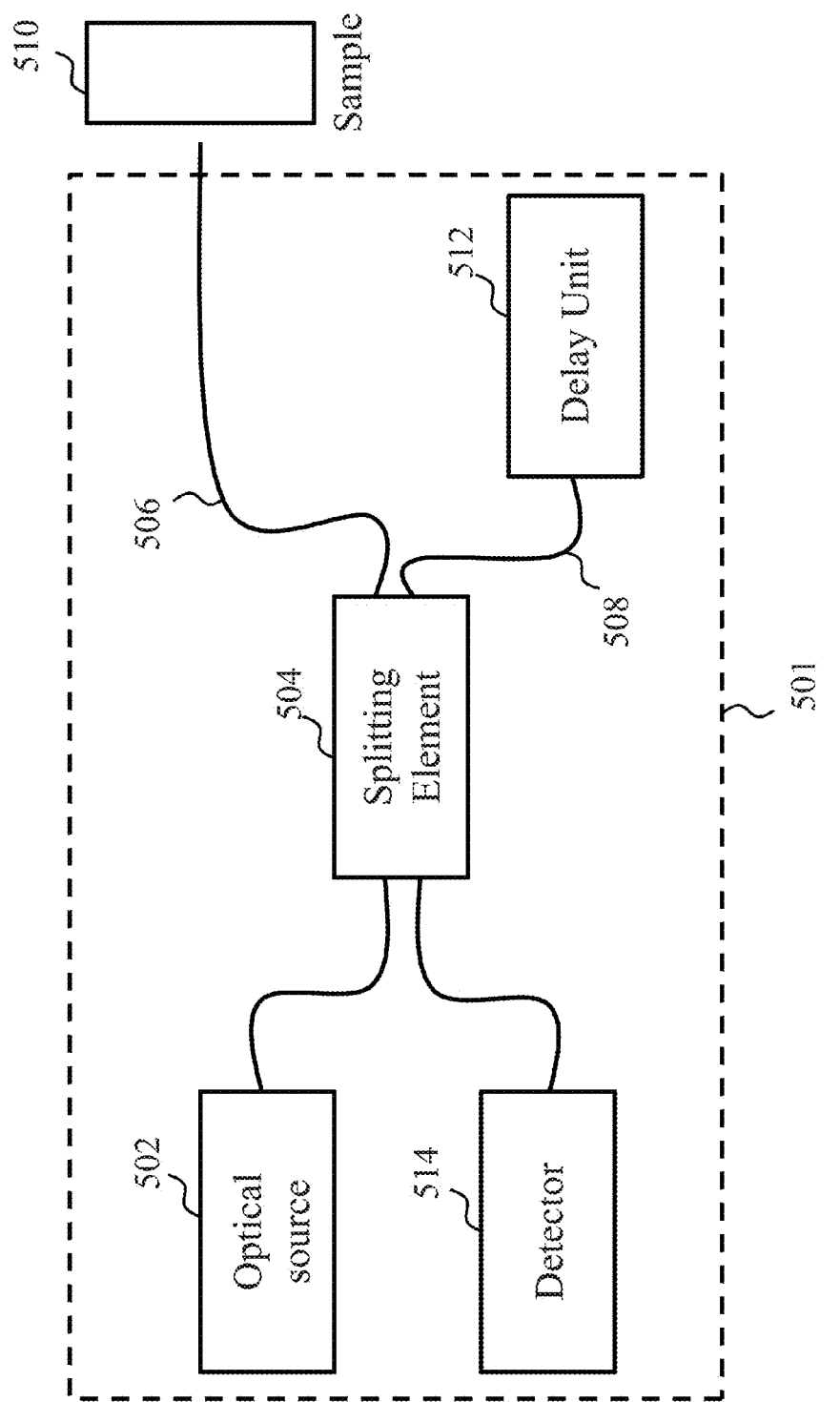

FIG. 5 illustrates a block diagram of an interferometric system, according to an embodiment.

Figure 6:
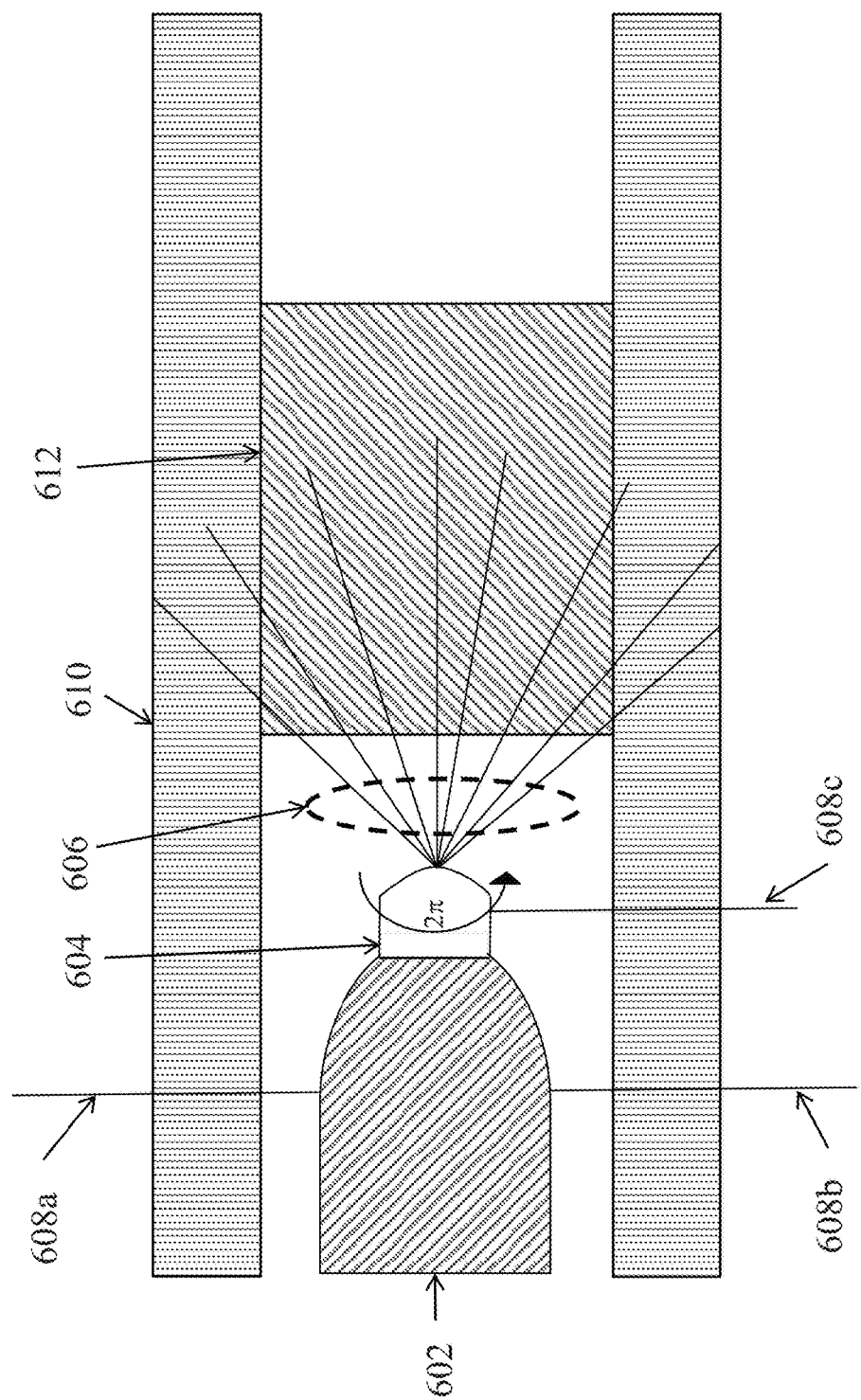

FIG. 6 illustrates interferometric scanning of an occlusion, according to an embodiment.

Figure 7:
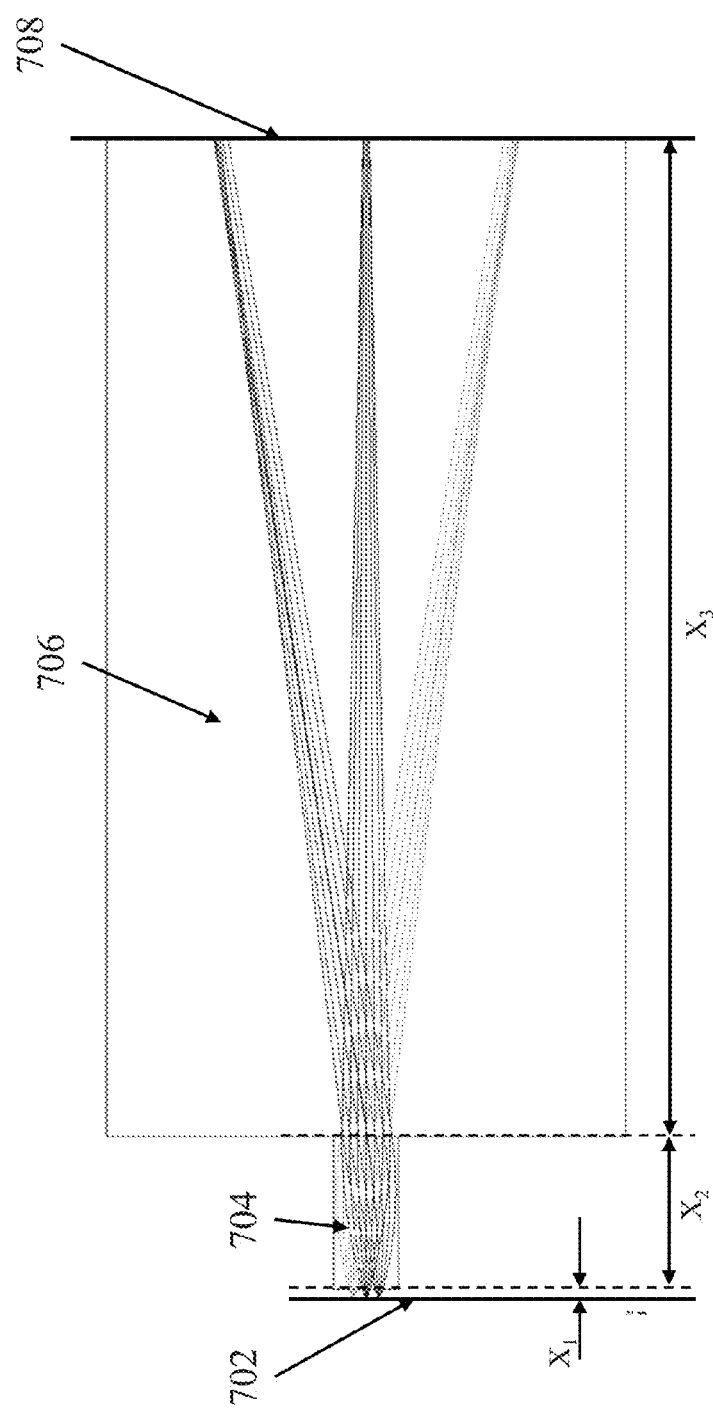

FIG. 7 displays an example ray-tracing simulation.

Figure 8:
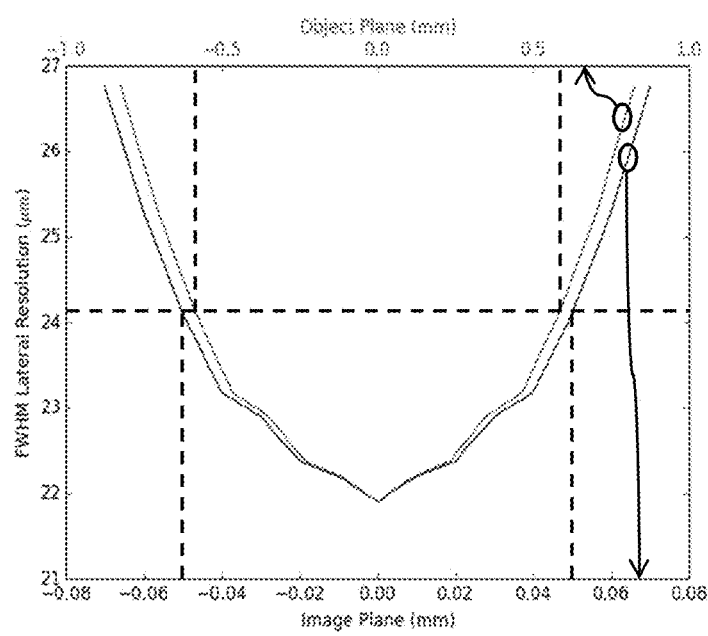

FIG. 8 displays simulation results of lateral resolution vs. field of view of an image plane and an object plane, according to an embodiment.

Figure 9:
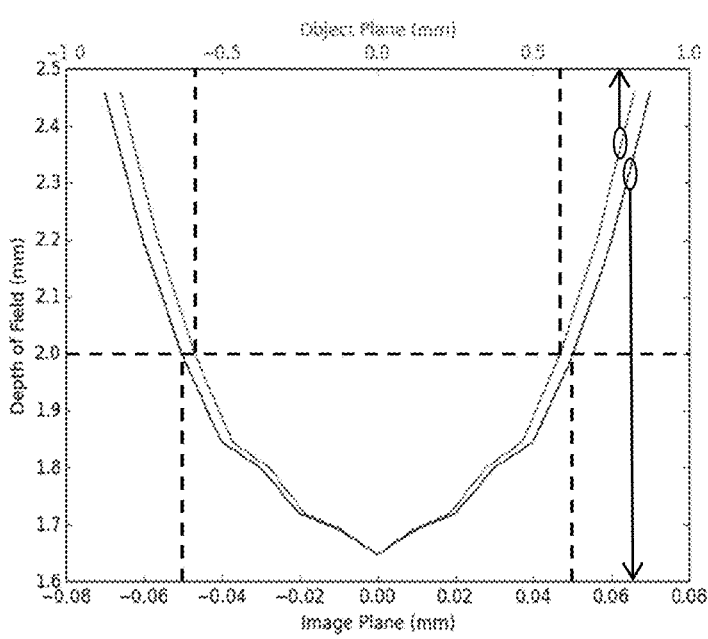

FIG. 9 displays simulation results of depth of field vs. field of view of an image plane and an object plane, according to an embodiment.

Figure 10:
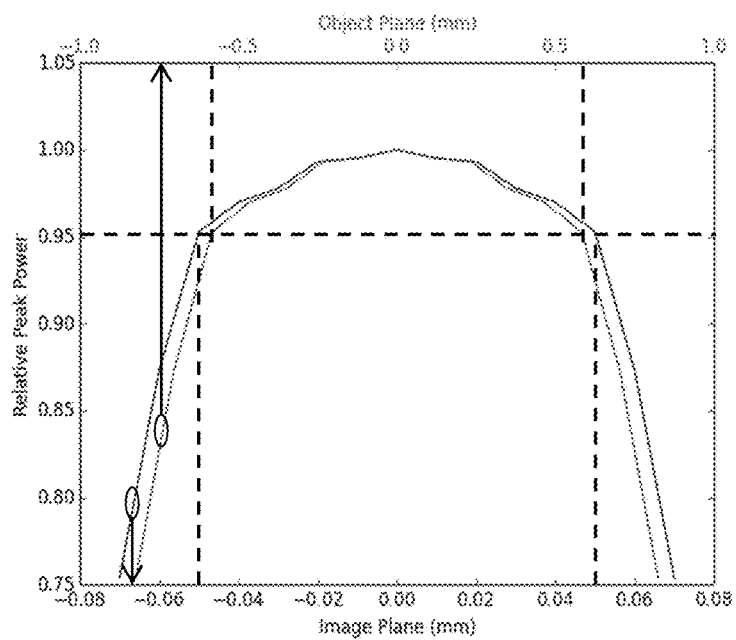

FIG. 10 displays simulation results of relative peak power vs. field of view of an image plane and an object plane, according to an embodiment.

Figure 11:
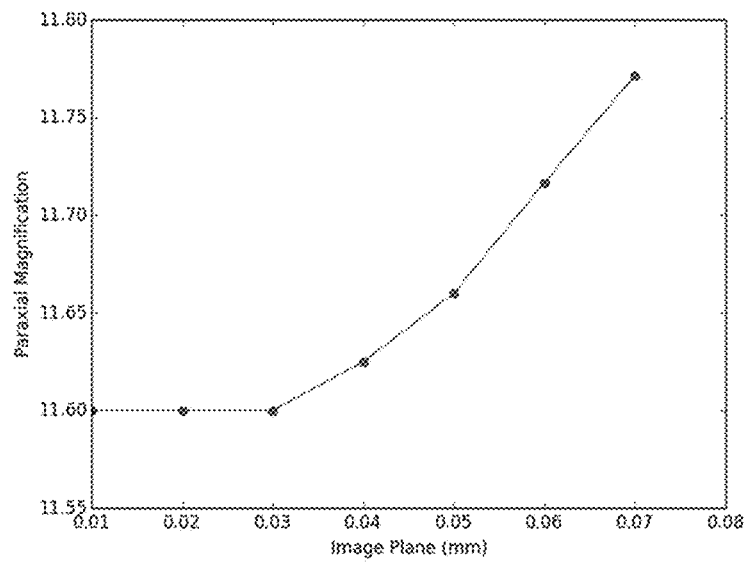

FIG. 11 displays simulation results of paraxial magnification vs. field of view of an image plane, according to an embodiment.

Figure 12:
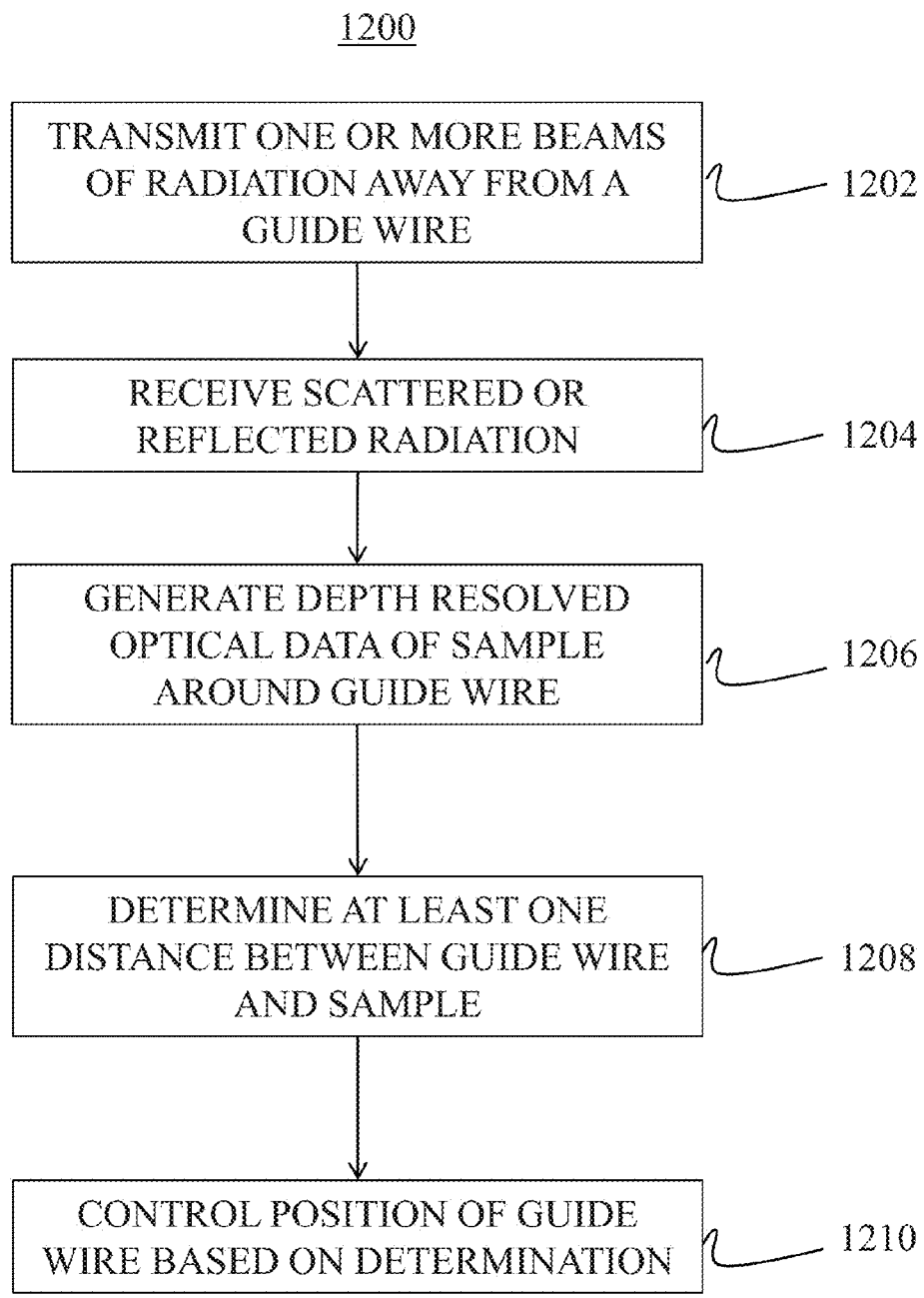

FIG. 12 depicts a method, according to an embodiment.

Figure 13:
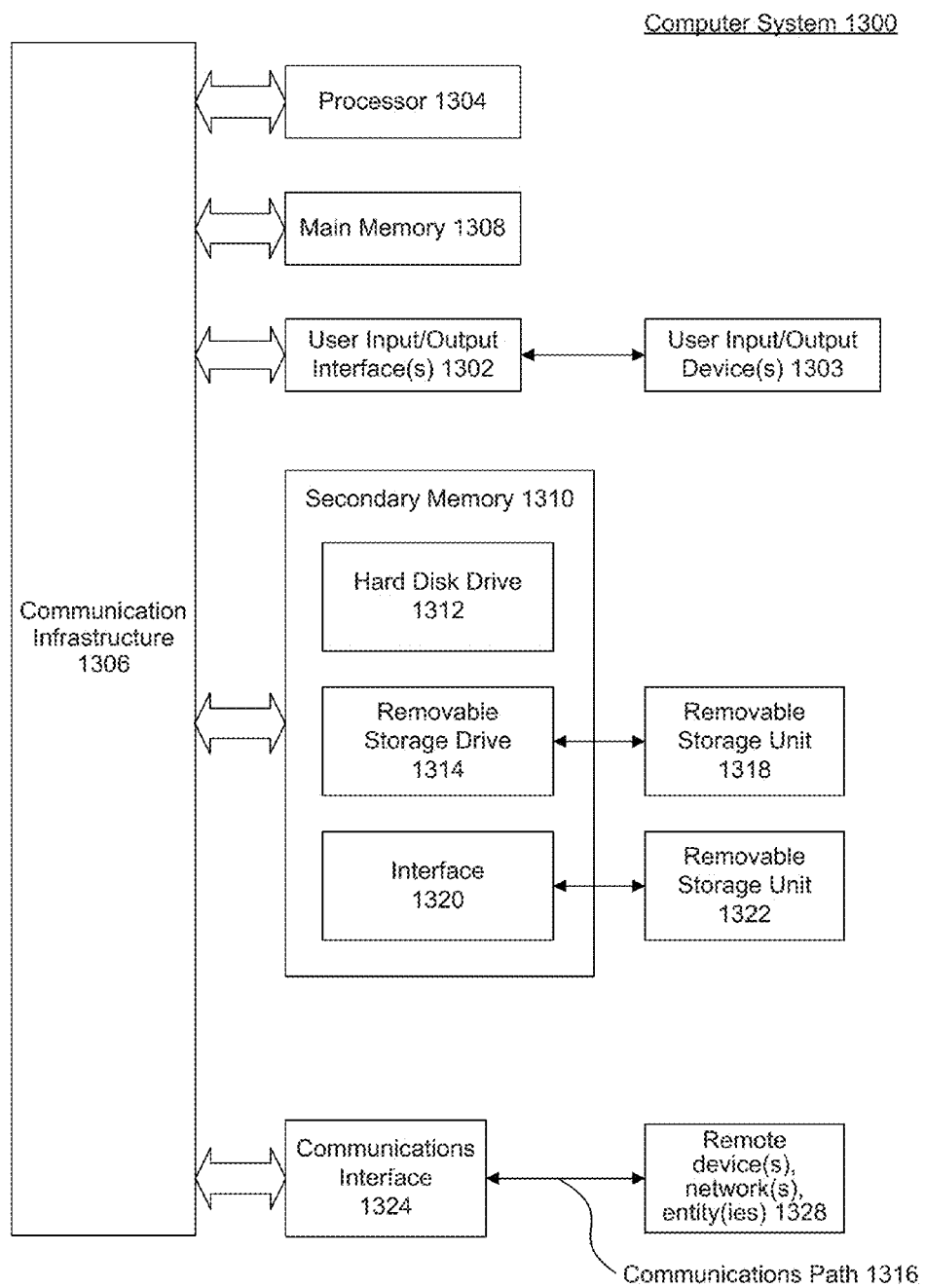

FIG. 13 illustrates an example computer system useful for implementing various embodiments.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to coronary occlusions, and the successful traversing of such occlusions, the embodiments described herein may be used for any other situations where a catheter or guide wire is guided through the body.

Described herein are embodiments of a catheter or guide wire for navigating through a vessel, such as an artery. The navigation is aided through the use of multiple view ports around the distal end of the catheter or guide wire through which beams of radiation are transmitted and received from the surrounding tissue. The beams of radiation are guided by patterned waveguides and are included in an interferometric system. As described herein, the interferometric technique used is optical coherence tomography (OCT). However, other interferometric techniques can be used as well. The OCT data may be used to generate images of the surrounding tissue and any occlusions blocking the path for the guide wire to travel. The data may also provide distance information between the guide wire and tissue and/or occlusion. This distance information may be utilized by a user or automatic feedback system to keep the guide wire or catheter substantially centered in the artery as it moves within the artery.

In one embodiment, the OCT data of the occlusion may be used to determine the location of one or more microchannels through the occlusion. The guide wire or catheter may be guided through the occlusion based on the locations of the microchannels. For example, the microchannels may indicate areas of the occlusion that are weaker and easier to puncture with the guide wire.

Herein, the terms "electromagnetic radiation," "light," and "beam of radiation" are all used to describe the same electromagnetic signals propagating through the various described elements and systems.

General Catheter Design

Figure 1:
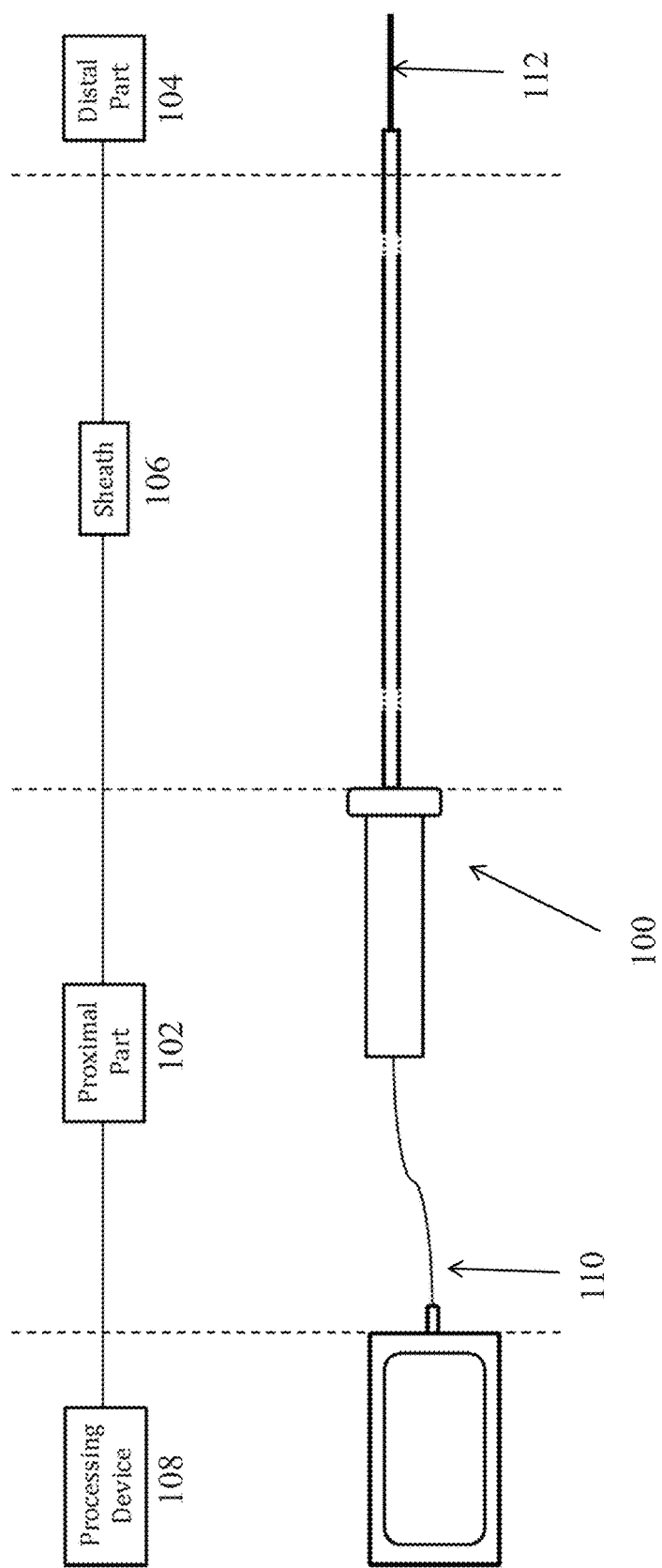
FIG. 1 illustrates a catheter with a guide wire, according to an embodiment.

FIG. 1 illustrates a catheter 100 according to an embodiment. Catheter 100 includes a proximal part 102, a distal part 104, and a sheath 106 coupled between proximal part 102 and distal part 104. In an embodiment, sheath 106 includes one or more radiopaque markers for navigation purposes. In one embodiment, catheter 100 includes a communication interface 110 between catheter 100 and a processing device 108. Communication interface 110 may include one or more wires between processing device 108 and catheter 100. In other examples, communication interface 110 is an interface component that allows wireless communication, such as Bluetooth, WiFi, cellular, etc. Communication interface 110 may communicate with one or more transceiver elements located within either proximal part 102 or distal part 104 of catheter 100.

In an embodiment, sheath 106 and distal part 104 are disposable. As such, proximal part 102 may be reused by attaching a new sheath 106 and proximal part 104 each time a new procedure is to be performed. In another embodiment, proximal part 102 is also disposable.

Proximal part 102 may house various electrical and optical components used in the operation of catheter 100. For example, a power supply may be included within proximal part 102 to supply electrical signals to various elements located in either proximal part 102 or distal part 104. As such, one or more conductive wires (or any electrical transmission medium) may lead from the power supply to distal part 104 within sheath 106. Furthermore, proximal part 102 may include an optical source for generating a beam of radiation. The optical source may include one or more laser diodes or light emitting diodes (LEDs). The beam of radiation generated by the optical source may have a wavelength within the infrared range. In one example, the beam of radiation has a central wavelength of 1.3 µm. The optical source may be designed to output a beam of radiation at only a single wavelength, or it may be a swept source and be designed to output a range of different wavelengths. The generated beam of radiation may be guided towards distal part 104 via an optical transmission medium connected between proximal part 102 and distal part 104 within sheath 106. Some examples of optical transmission media include single mode and multimode optical fibers and integrated optical waveguides. In one embodiment, the electrical transmission medium and the optical transmission medium are provided by the same hybrid medium allowing for both electrical and optical signal propagation.

In an embodiment, proximal part 102 includes one or more components of an interferometer in order to perform OCT using the light generated from the optical source. Further details of an interferometer system are discussed with reference to FIG. 5. Due to the nature of interferometric data analysis, in an embodiment the optical transmission medium used for guiding the light to and from distal end 104 does not affect the state and degree of light polarization. In another embodiment, the optical transmission medium affects the polarization in a constant and reversible way.

In an embodiment, a guide wire 112 extends from distal part 104 of catheter 100. Guide wire 112 may be used to help navigate catheter 100 through smaller vessels. According to various embodiments herein, optical elements may be placed in distal part 104 of catheter 100, and/or within a distal section of guide wire 112 for performing OCT analysis of the surrounding tissue.

Proximal part 102 may include further interface elements with which a user of catheter 100 can control the operation of catheter 100. For example, proximal part 102 may include a deflection control mechanism that controls a deflection angle of distal part 104 or of guide wire 112. The deflection control mechanism may require a mechanical movement of an element on proximal part 102, or the deflection control mechanism may use electrical connections to control the movement of distal part 104 or guide wire 112. Proximal part 102 may include various buttons or switches that allow a user to control when optical data is acquired from distal end 104 and/or guide wire 112.

Guide Wire OCT Embodiments

Figure 2A:
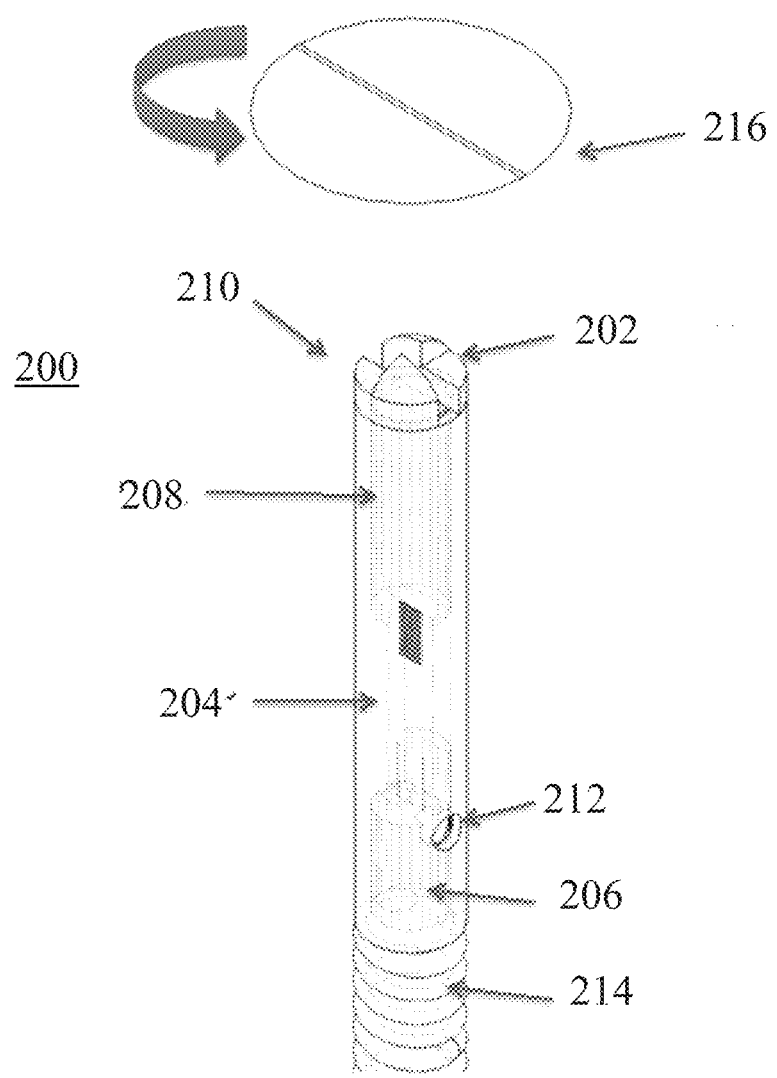
FIGS. 2A-2B illustrate elements within a guide wire, according to embodiments.
Figure 2B:
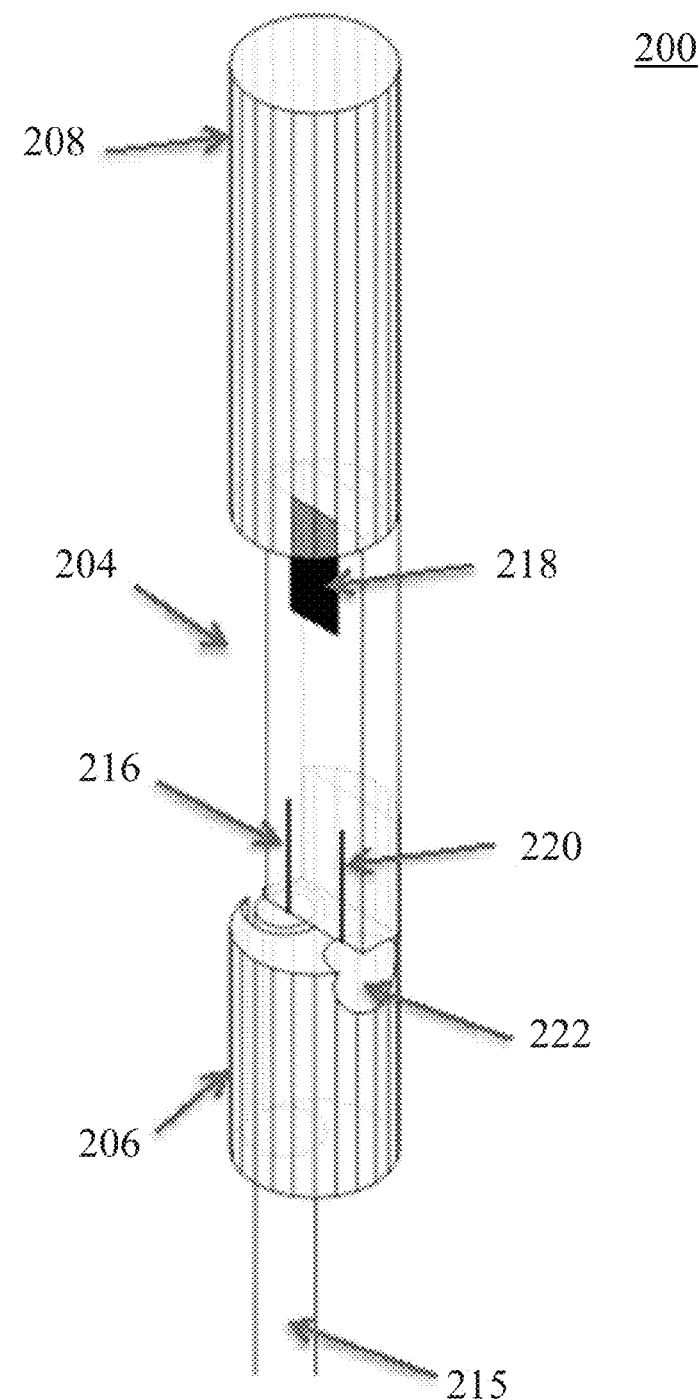

FIGS. 2A and 2B illustrate an embodiment of a guide wire 200 that includes optical elements near a tip of guide wire 200. FIG. 2A illustrates various elements integrated at a distal end of guide wire 200 and encapsulated within a housing. FIG. 2B illustrates a more detailed example of the integrated elements without the housing. In one example, guide wire 200 includes one or more cutting lips 202 at its tip. Cutting lips 202 may be used to help guide wire 200 slice through an occlusion that blocks the path of guide wire 200 within an artery. In another example, guide wire 200 includes a conical drill shape at its tip. Within guide wire 200, a multiplexing unit 204 is included and coupled to light received from optical fiber 215, according to an embodiment. Optical fiber 215 transmits source light generated from an optical source, and may also be designed to receive light collected from around guide wire 200. Other optical fibers may be included as well for transmitting and/or receiving light, such as in a bundle of fibers.

According to an embodiment, optical fiber 215 is single-mode for the operation wavelength. Due to the highly scattering nature of tissues commonly involved when using a guide wire to navigate through blood vessels, the operation wavelength may be centered at 1.3 micrometers because of reduced scattering. Depending on the application, other operation wavelengths may include 800 nm or 1050 nm. Optical fiber 215 may include reduced cladding (80 µm) in order to minimize its diameter and to minimize the acceptable bend radius of optical fiber 215.

Multiplexing unit 204 may include an input waveguide 216 for receiving light guided from optical fiber 215. A molded element 206 may be provided to help align optical fiber 215 with input waveguide 216 of multiplexing unit 204. Multiplexing unit 204 provides one or more beams of radiation to a plurality of waveguides 218 that are used to transmit light in a forward-looking direction of guide wire 200, according to an embodiment. This forward-looking direction may be substantially parallel to an axis extending along a length of the guide wire and passing through a center of the guide wire. Plurality of waveguides 218 may be patterned or otherwise provided on a flexible substrate. The flexible substrate may be rolled into a particular shape to fit within the tight confines of guide wire 200. For example, the flexible substrate that includes plurality of waveguides 218 may be rolled into an annulus shape. Plurality of waveguides 218 may provide multiple scanning beams of light for performing OCT in front of guide wire 200. In one example, a substantially straight scanning line 216 is created based on light outputs from plurality of waveguides 218 through a machined opening 210 at the tip of guide wire 200. Plurality of waveguides 218 may be equally spaced apart from one another. For example, each of plurality of waveguides 218 may be spaced 50 µm from one another. In an embodiment, one or more optical elements 208 are included between plurality of waveguides 218 and opening 210. Optical elements 208 may include any number of mirrors and/or modulators used to at least one of focus and steer the beam of light. In one example, optical elements 208 includes a graded index refraction (GRIN) lens.

In one embodiment, a side-imaging waveguide 220 is included in order to transmit and/or collect beams of radiation from different angles around guide wire 200. For example, side-imaging waveguide 220 may direct a beam of radiation towards a reflector 222. Reflector 222 directs the beam of light through an imaging port 212 and away from guide wire 200. The beam of light may be transmitted at a non-zero angle relative to an axis extending along a length of the guide wire and passing through a center of the guide wire. Scattered or reflected light can also be received through imaging port 212. In this way, lateral imaging of tissue surrounding guide wire 200 can be achieved. More than one imaging port 212 and side-imaging waveguide 220 can be included within guide wire 200 to take OCT images at various angles. Plurality of waveguides 218 provide imaging capability of tissue directly in front of guide wire 200, according to an embodiment.

According to an embodiment, at least one of plurality of waveguides 218 transmits a beam of radiation away from guide wire 200 and at least one of plurality of waveguides 218 receives a beam of scattered and/or reflected radiation from a sample.

Multiplexing unit 204 may include associated electronics that provide control signals to various modulating elements of multiplexing unit 204 in order to direct light through various waveguides such as side-imaging waveguide 220 and plurality of waveguides 218. Multiplexing unit 204 may use any multiplexing method that allows for the separation of contributions from the light collected around guide wire 200. One such multiplexing method is time-domain multiplexing, in which multiplexing unit 204 switches between different output waveguides in a controlled manner, so that at a given time only one associated waveguide is active. Another suitable multiplexing method is frequency-domain multiplexing, in which light traversing each of the waveguides is modulated in such a way that the time-frequency behavior of signals corresponding to different waveguides can be differentiated by a processing device. Coherence-domain multiplexing may also be used in multiplexing unit 204, by introducing a different group delay to the light traversing each waveguide, so that the signals corresponding to different waveguides appear at different coherence positions and can be therefore differentiated by a processing device. In an embodiment, these methods are non-exclusive and can be combined in order to find the best design compromise. Based on the multiplexing method used, multiplexing unit 204 may be a passive element or electrically driven. Some of the multiplexing methods, like coherence-domain multiplexing, do not require any electrical actuation of multiplexing unit 204. Thus, in an embodiment, implementations based on coherence-domain multiplexing do not require electrical transmission media for control signals.

In one embodiment, multiplexing unit 204 is produced on a silicon photonics optical chip using a network of thermo-electric optical switches. Other suitable materials for use in multiplexing unit 204 include, for example and without limitation, silicon nitride, silicon dioxide, oxinitride, lithium niobate, III-V semiconductor materials, silicon carbide and optical grade polymers. Other modulation effects to support the optical switching operation include the electro-optic effect, charge carrier density effects, photo-mechanical effects, liquid crystal based refractive index modulation, etc. The multiplexing function may also be obtained through microelectromechanical (MEMS) devices in as far as miniaturization and packaging constraints can be met.

In an embodiment, multiplexing unit 204 is fabricated upon a flexible substrate. Multiplexing unit 204 may be fabricated on a same flexible substrate as plurality of waveguides 218. A process for forming the optical elements upon a flexible substrate includes a substrate transfer post-processing step applied to Silicon on Insulator (SOI) chips or wafers, as described in more detail in U.S. Pat. No. 9,062, 960, the disclosure of which is incorporated by reference herein in its entirety. In an embodiment, the resulting flexible device is thinner (<100 μm) than the starting thickness (500-700 μm). Multiplexing unit 204 may be implemented by an optical integrated chip that is partly flexible.

In an embodiment, guide wire 200 includes a braided coil 214 leading up to the various optical elements disposed near the tip. Braided coil 214 may be designed to transmit torque during a rotation of guide wire 200. Rotating guide wire 200 may be helpful for providing a complete image around guide wire 200. The rotation also will rotate the forward-looking radiation beams to provide a wider view of a sample surface in front of guide wire 200 as illustrated in FIG. 2A. Rotation of guide wire 200 may be performed manually by an operator, or by electrically driven actuators. Upon controlled rotation, the forward-facing opening 210 can be used to sample a 3D volume in front of the tip of guide wire 200, while imaging port 212 provides a rotational scan showing the relative position of guide-wire 200 within an artery, according to an embodiment.

During rotation, guide wire 200 may accumulate strain. If rotation is kept at a constant frequency, fatigue can be minimized while rotation of the tip reaches steady state after a few turns. To monitor torsional loads, one or more strain gauges may be included on guide wire 200. Thus, by combining an appropriate model of strain accumulation and the feedback obtained from strain gauges, appropriate location of the various beams of radiation transmitted from guide wire 200 can be achieved within a 3D model. Other solutions enabling torsion monitoring by optical means can be exploited. In an embodiment, the use of distributed Fiber Bragg Gratings (FBGs) defined along optical fiber 215 allows for sensing the stress along guide wire 200 if both optical fiber 215 and guide wire 200 are in conjunction. The distributed strain sensors may be interrogated at wavelengths different from that used by the OCT system, thus avoiding optical crosstalk. Alternatively, guide wire 200 may be supported by a catheter with a steerable tip which would assist in navigation through tortuous vascularity. This catheter may be provided with OCT capabilities as well, and is described herein.

Catheter OCT Embodiments

FIG. 3 illustrates a view of catheter 300, according to an embodiment. Catheter 300 includes elements involved in the transmission of radiation for imaging around catheter 300. Catheter 300 also substantially surrounds a guide wire 302 that passes through a center axis of catheter 300. Note that a housing which would contain the various optical elements is not included in FIG. 3 for clarity.

According to an embodiment, catheter 300 includes a distal section having a waveguide input 304, a multiplexing unit 306, a flexible substrate 308 that includes a plurality of waveguides 310, and a plurality of optical elements 312. One or more optical elements 312 may be included within a molded element 314 to substantially align one or more optical elements 312 with outputs from plurality of waveguides 310. Each individual element of one or more optical elements 312 may be designed to feature a different optical performance. For example, properties such as the depth of field (DoF), resolution, working distance (WD), and beam direction (e.g., beam steering) can be discretely adjusted for each optical element. Other optical elements, such as lenses, mirrors, etc. may be included as well without deviating from the scope or spirit of the invention.

Each of the elements included within catheter 300 may operate in a similar fashion to corresponding elements previously described as being included within a guide wire. For example, waveguide input 304 may be similar to optical fiber 215, multiplexing unit 306 may be similar to multiplexing unit 204, plurality of waveguides 310 may be similar to plurality of waveguides 218, and one or more optical elements 312 may be similar to one or more optical elements 208. As can be seen from the illustration in FIG. 3, both multiplexing unit 306 and flexible substrate 308 may be wrapped in an annulus shape substantially around guide wire 302. Plurality of waveguides 310 may guide beams of radiation via one or more optical elements 312 in a forward-looking direction as guide wire 302 moves through a vessel, such as an artery.

According to an embodiment, at least one of plurality of waveguides 310 transmits a beam of radiation away from catheter 300 and at least one of plurality of waveguides 310 receives a beam of scattered and/or reflected radiation from a sample.

Catheter 300 may be used to deliver stents which act as scaffolds to maintain blood flow through blocked blood vessels. To maximize coupling efficiency between waveguide input 304 and multiplexing unit 306, focusing optics may be used. The focusing optics may be included on the flexible substrate of multiplexing unit 306 or could be their own elements spaced between waveguide input 304 and multiplexing unit 306. Alternatively, lensed optical fibers can provide a more compact solution providing mode matching between an input/output waveguide patterned on a flexible substrate and the light propagating medium without the use of extra optical elements. Similar to the guide wire embodiments discussed previously, multiple view-ports may be implemented by making use of various waveguides to direct light at different angles from catheter 300. In one example, a micro-optics-based lens array can be included for transmitting and receiving beams of radiation from various view ports around catheter 300. The optical performance of each focusing element included in the array may be independently designed in order to adjust angle of incidence, depth of focus and lateral resolution among others.

FIGS. 4A and 4B illustrate a side view and front-facing view respectively of catheter 300, according to an embodiment. The side view illustrated in FIG. 4A shows how guide wire 302 may protrude out further from the distal end of catheter 300. Catheter 300 is also shown to include an optical fiber 402 coupled to some kind of waveguide as part of multiplexing unit 306. Multiplexing unit 306 may be designed to receive a beam of radiation from optical fiber 402 and provide multiple beams of radiation to be guided via plurality of waveguides 310. FIG. 4B illustrates how optical fiber 402 may couple to one portion of multiplexing unit 306. Multiplexing unit 306 is illustrated as wrapped in an annulus shape within catheter 300 and substantially around guide wire 302.

In one embodiment, the elements used to provide OCT imaging around catheter 300 and guide wire 302 are only contained within catheter 300. In another embodiment, the elements used to provide OCT imaging around catheter 300 and guide wire 302 are only contained within guide wire 302. In another embodiment, the elements used to provide OCT imaging around catheter 300 and guide wire 302 are contained within both catheter 300 and guide wire 302.

In an embodiment, flexible electronics can be used to facilitate electrical driving of multiplexing unit 306. In one example, a printed circuit board (PCB) may include the necessary driving electronics and be attached to a photonic integrated chip (PIC), by means of, for example, flip chip technology. Both the PCB and PIC may then be subjected to a flexibilization process, resulting in a rolled stack of materials as illustrated generally in FIG. 3, where multiplexing unit 306 and flexible substrate 308 are coupled together. In this embodiment, a lensed fiber may be used as waveguide input 304 to couple light in and out. In one embodiment, a hybrid cable containing the aforementioned lensed fiber and electrical wires propagating the signals driving multiplexing unit 306 is used. In other embodiment, both the lensed fiber (or any other light transmission media such as flexible planar lightwave circuits (PLCs)) and the electrical wires are assembled separately. For clarifying purposes, the array is separated from the output of the flexible chip. However, it may be attached to the output waveguides of the flexible PIC in a manner as known to one of skill in the art. In other embodiments, different types of focusing optics solutions can be used. Note that for simplicity, the micro-catheter sheath is not shown in FIG. 4.

Interferometry System Embodiment

Various embodiments of the present application include an OCT-based imaging system for optical interrogation of tissue. FIG. 5 illustrates an example OCT system 501 for imaging a sample 510, according to an embodiment. For example, sample 510 may be a portion of an atrial wall. A delay unit 512 may include various light modulating elements. These modulating elements may perform phase and/or frequency modulation to counteract undesired optical effects in the light, and to select one or more depths of sample 510 to be imaged. The use of the term "light" may refer to any range of the electromagnetic spectrum. In an embodiment, the term "light" refers to infrared radiation at a wavelength of about 1.3 μm.

OCT system 501 further includes an optical source 502, a splitting element 504, a sample arm 506, a reference arm 508, and a detector 514. In the embodiment shown, delay unit 512 is located within reference arm 508. However, it should be understood that delay unit 512 may instead be located in sample arm 506. Alternatively, various elements of delay unit 512 may be present in both sample arm 506 and reference arm 508. For example, elements of delay unit 512 that introduce a variable delay to the light may be located in sample arm 506, while elements that modulate different polarization modes of the light may be located in reference arm 508. In one example, sample arm 506 and reference arm 508 are optical waveguides, such as patterned waveguides or optical fibers. In an embodiment, all of the components of OCT system 501 are integrated onto a planar lightwave circuit (PLC). In another embodiment, at least the components within delay unit 512 are integrated on the same substrate of a PLC. Other implementations may be considered as well, such as, for example, fiber optic systems, free-space optical systems, photonic crystal systems, etc. The various optical components, such as splitting element 504, sample arm 506, reference arm 508, and delay unit 512, may be integrated on the same substrate as the multiplexing unit described previously in either the catheter or guide wire embodiments. In another embodiment, such optical elements are integrated on their own substrate and may be included anywhere within catheter 100.

It should be understood that OCT system 501 may include any number of other optical elements not shown for the sake of clarity. For example, OCT system 501 may include mirrors, lenses, gratings, splitters, micromechanical elements, etc., along the paths of sample arm 506 or reference arm 508.

Splitting element 504 is used to direct light received from optical source 502 to both sample arm 506 and reference arm 508. Splitting element 504 may be, for example, a bi-directional coupler, an optical splitter, or any other modulating optical device that converts a single beam of light into two or more beams of light.

Light that travels down sample arm 506 ultimately impinges upon sample 510. Sample 510 may be any suitable sample to be imaged, such as tissue. The light scatters and reflects back from various depths within sample 510, and the scattered/reflected radiation is collected back into sample arm 506. In another embodiment, the scattered/reflected radiation is collected back into a different waveguide than the transmitting waveguide. The scan depth may be chosen via the delay imposed on the light within delay unit 512. In an embodiment, sample arm 506 is implemented as optical fiber 215 from the above-described guide wire embodiment and/or as optical fiber 402 from the above-described catheter embodiment.

Light within sample arm 506 and reference arm 508 is recombined before being received at detector 514. In the embodiment shown, the light is recombined by splitting element 504. In another embodiment, the light is recombined at a different optical coupling element than splitting element 504. Detector 514 may include any number of photodiodes, charge-coupling devices, and/or CMOS structures to transduce the received light into an electrical signal. The electrical signal contains depth-resolved optical data related to sample 510 and may be received by a processing device for further analysis and signal processing procedures. As used herein, the term "depth-resolved" defines data in which one or more portions of the data related to specific depths of an imaged sample can be identified.

In an embodiment, optical source 502, detector 514 and delay unit 512 are located within proximal part 102 of catheter 100. Splitting element 504 and at least part of one or both of sample arm 506 and reference arm 508 may be located in either proximal part 102 or distal part 104 of catheter 100. In another embodiment, all of the elements of OCT system 501 are located in distal part 104 of catheter 100. Optical source 502 may include one or more light emitting diodes (LEDs) or laser diodes. For example, LEDs may be used when performing time domain and/or spectral domain analysis, while tunable lasers may be used to sweep the wavelength of the light across a range of wavelengths.

OCT system 501 is illustrated as an interferometer design similar to a Michelson interferometer, according to an embodiment. However, other interferometer designs are possible as well, including Mach-Zehnder or Mireau interferometer designs.

Imaging Technique Embodiments

FIG. 6 illustrates the use of OCT imaging around a catheter and guide wire system to aid in the navigation of the catheter and guide wire through a vessel, according to an embodiment. As an example, FIG. 6 illustrates an arterial wall 610 and an occlusion 612 blocking the path of catheter 602 and guide wire 604.

Multiple OCT scans based on transmitting a beam of radiation and receiving scattered and/or reflected beams of radiation from the surrounding tissue are illustrated. For example, a plurality of interferometry scans 606 may emanate from a distal end of guide wire 604. Plurality of interferometry scans 606 may be arranged such that a straight line of any sample in front of guide wire 604 is imaged. In another example, by arranging the angle of the looking-forward interferometry scans 606 appropriately, truncated cone images may interlace, thus increasing resolution by a factor of 2 after a rotation is made of guide wire 604. Guide wire 604 may be rotated about an axis passing through a center of guide wire 604, as illustrated in FIG. 6 and described previously.

The rotation of guide wire 604 to gain 3D images of part of a volume in front of guide wire 604, and potentially 2D images of a portion of arterial wall 610, can be introduced by a mechanical actuator placed outside the body and in physical connection with a proximal end of guide wire 604. Such an actuator may be designed to produce a continuous rotation of guide wire 604 with at least 180 degrees range. If the rotation speed is moderate (one or two images per second) and the rotation is not free-running, but rather applied in a periodic oscillating way, a rotational coupler may be avoided at the distal end of guide wire 604. Transmission of the applied torque to the distal end of guide wire 604 may be considered since limited stiffness of the wire may require a constant rotation direction.

Images are also captured of arterial wall 610, surrounding at least a portion of catheter 602 and/or guide wire 604. These images are achieved from additional interferometry scans 608a-c extending at different angles (e.g., right angles) from the main body of catheter 602 and guide wire 604. For example, guide wire 604 may perform interferometry scan 608c by directing light via a spherical reflector away from guide wire 604 at a different angle than interferometry scans 606. Also, catheter 602 may perform interferometry scans 608a-b by directing light via one or more spherical reflectors away from catheter 602 at a different angle than interferometry scans 606. By rotating guide wire 604 (and catheter 602) as illustrated in FIG. 6, images can be captured of a section of arterial wall 610 that substantially surrounds catheter 602 and/or guide wire 604.

The OCT data that can be collected from any of interferometry scans 608a-c and 606 may be used to determine various distances and properties of the surrounding tissue, according to some embodiments. For example, interferometry scans 608a-b may be used to determine a distance between catheter 602 and arterial wall 610, while interferometry scan 608c may be used to determine a distance between guide wire 604 and arterial wall 610. An operator of catheter 602 may use the distance information to control the placement of catheter 602 to substantially align within a center of the artery as catheter 602 moves along a length of the artery. In another example, the distance information is used as a control signal in a feedback configuration to automatically control the position of catheter 602 within the artery.

The more forward-looking interferometry scans 606 may be used to gather distance and morphology information regarding occlusion 612, according to an embodiment. For example, the OCT data extracted from interferometry scans 606 may be used to determine the presence of micro-channels present within occlusion 612. These micro-channels may present a path of least resistance for boring through occlusion 612 with guide wire 604.

Some biological polymers such as collagen are substantially birefringent. Collagen is particularly present in the tunica adventitia in the arterial wall, the outermost layer of blood vessels. Thus, polarization-sensitive imaging may be introduced to increase contrast between the imaged structures. In another example, blood may flow though any micro-channels present within occlusion 612, and therefore Doppler imaging may contribute to enhance these micro-channel structures.

Optical Simulation Results

FIG. 7 illustrates a ray-tracing simulation of a plurality of interferometry scans originating from a device and propagating through a medium. The beams originate from waveguide output plane 702 and pass through a lens 704, such as a GRIN lens. After traversing lens 704, the beams propagate through medium 706 and impinge upon sample interface 708. For the simulation illustrated, the refractive index of medium 706 is set to 1.33 at a wavelength of 1.32 µm to model human blood. Also the distances between various optical planes denoted as $X_1$, $X_2$, and $X_3$ are each set to achieve Gaussian beam profiles at sample interface 708 having a full width half maximum (FWHM) of about 21.9 µm (e.g., lateral resolution of about 22 µm.) In this simulation example, $X_1=37$ µm, $X_2=534$ µm, and $X_3=3.498$ mm. The three ray traces originate at waveguide output plane 702 and are spaced such that they are transmitted from waveguides that are 50 µm apart from one another.

As shown in the simulation, the working distance between the end of the guide wire and sample interface 708 is about 3.5 mm. A glass spacer may be attached to an end of the guide wire to adjust the working distance. For example, it may be desirable to adjust the working distance to be half of the depth of field (DOF).

FIGS. 8-11 provide further example simulation results of various parameters based on the ray-tracing environment of FIG. 7. FIG. 8 shows simulation results for the lateral resolution (FWHM) as a function of the field of view (FOV) in the object plane (sample interface 708) and image plane ($X_1$ distance from waveguide output plane 702), relative to a center position. According to an embodiment, and as derived from the results shown in FIG. 8, the larger the FOV on the image plane, the lower the lateral resolution. Therefore, a minimum lateral resolution figure will limit the FOV in practice. Assuming a maximum degradation of 10% over the designed FWHM (24.09 µm), the FOV becomes approximately 1.16 mm, which represents 0.1 mm in the image plane. Therefore, the output waveguides position should be properly distributed along ±0.05 mm from a center position in order to reach continuous scanning on the object plane.

FIG. 9 shows the relationship between the DOF and the FOV in the object plane and in the image plane. As illustrated in FIG. 9, at the center position of 21.9 µm, FWHM is obtained, which represents a DOF of 1.64 mm. The loss of lateral resolution results in an enlargement of the DOF. Assuming a FOV on the object plane of 1.16 mm, the DOF becomes 2 mm in the vicinity of the FOV limits.

FIG. 10 shows the relative peak power as a function of the FOV in the image plane and the object plane. Results shown in FIG. 10 may be understood as an indicator of the beam distortion. The peak power is reduced when increasing the FOV because secondary lobules appear. In this case, the peak power is reduced by less than the 5% assuming a FOV of 1.16 mm in the object plane.

FIG. 11 shows the paraxial magnification as a function of the image plane measured from the center position to the image plane limit. According to an embodiment, the paraxial magnification of a GRIN lens does not show a flat profile as a function of the field of view. In fact, the paraxial magnification stops being flat when considering a FOV on the image plane larger than 0.06 mm as depicted in FIG. 11. This effect may be corrected under certain conditions by acting on the profile of the refractive index of the GRIN lens.

Example Method of Operation

FIG. 12 illustrates an example method 1200 for controlling the position of a guide wire. The guide wire may be within an artery and used to bore through an occlusion within the artery. Method 1200 may be performed by various components of guide wire 200 and/or catheter 300 in conjunction with processing device 108.

At block 1202, one or more beams of radiation are transmitted away from a guide wire, according to an embodiment. The beams of radiation may be transmitted away using a plurality of waveguides patterned onto a flexible substrate. The waveguides may be arranged along with other optical elements to transmit the beams of radiation in a forward-facing direction substantially parallel to an axis extending along a length of the guide wire and passing through a center of the guide wire. Some of the waveguides may be arranged to transmit beams of radiation at non-zero angles with respect to the axis and away from the guide wire.

At block 1204, scattered or reflected radiation is received, according to an embodiment. This scattered radiation may be received by the same plurality of waveguides used to transmit the beams of radiation, or by different waveguides. The radiation may be scattered or reflected from a sample around the guide wire.

At block 1206, depth-resolved optical data is generated based on the beams of radiation received from the sample around the guide wire. For example, a detector may generate an electrical signal based on the received beams of radiation. The generated electrical signal may then be received by a processing device for further analysis and signal processing to perform certain actions and/or generate models based on the depth-resolved optical data. An image of the sample surface, as well as 3-D images through a depth of the sample, may be generated from the depth-resolved optical data. The image may be provided to an operator of the guide wire via a user interface such as a display.

At block 1208, at least one distance is determined between the guide wire and the sample, according to an embodiment. This distance may be associated with a distance to an arterial wall surrounding the guide wire, or to a distance between a front of the guide wire and an occlusion within the artery. The distance(s) may be determined based on the depth-resolved optical data. The distances may be used to determine a relative location of the guide wire.

At block 1210, a position of the guide wire is controlled based on the determination, according to an embodiment. The distance information may be relayed to an operator of the guide wire via any suitable user interface (e.g., displace, audio cues, etc.) The operator may then control the guide wire manually based on the distance information to keep the guide wire centered within an artery. In another example, a feedback control system is used to automatically correct the position of the guide wire based on the distance information. The guide wire may be controlled to maintain a position within a center of the artery as the guide wire moves along a length of the artery.

Many other actions may be performed as part of method 1200. For example, the guide wire may be controlled to traverse the occlusion in its path using one or more cutting lips disposed at the end of the guide wire. In another example, the guide wire may heat a portion of the occlusion to aid in passing through the occlusion. Heat may be generated by passing a current through one or more electrodes positioned on an outer surface of the guide wire.

Method 1200 may also include determining a location of one or more micro-channels in the occlusion based on the depth-resolved optical data. The micro-channels may be as small as 50 µm in diameter. Once the location of one or more of these micro-channels is established, the guide wire may be controlled to traverse the occlusion based on the location of the one or more micro-channels. For example, the presence of micro-channels may indicate a structural weakness in the occlusion and could identify a path of lower resistance for boring through the occlusion with the guide wire.

Example Computer System Embodiment

Various processing methods and other embodiments described thus far can be implemented, for example, using one or more well-known computer systems, such as computer system 1300 shown in FIG. 13. In an embodiment, computer system 1300 may be an example of processing device 108 illustrated in FIG. 1.

Computer system 1300 includes one or more processors (also called central processing units, or CPUs), such as a processor 1304. Processor 1304 is connected to a communication infrastructure or bus 1306. In one embodiment, processor 1304 represents a field programmable gate array (FPGA). In another example, processor 1304 is a digital signal processor (DSP).

One or more processors 1304 may each be a graphics processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data common to computer graphics applications, images and videos.

Computer system 1300 also includes user input/output device(s) 1303, such as monitors, keyboards, pointing devices, etc., which communicate with communication infrastructure 1306 through user input/output interface(s) 1302.

Computer system 1300 also includes a main or primary memory 1308, such as random access memory (RAM). Main memory 1308 may include one or more levels of cache. Main memory 1308 has stored therein control logic (i.e., computer software) and/or data.

Computer system 1300 may also include one or more secondary storage devices or memory 1310. Secondary memory 1310 may include, for example, a hard disk drive 1312 and/or a removable storage device or drive 1314. Removable storage drive 1314 may be a floppy disk drive, a magnetic tape drive, a compact disc drive, an optical storage device, tape backup device, and/or any other storage device/drive.

Removable storage drive 1314 may interact with a removable storage unit 1318. Removable storage unit 1318 includes a computer usable or readable storage device having stored thereon computer software (control logic) and/or data. Removable storage unit 1318 may be a floppy disk, magnetic tape, compact disc, Digital Versatile Disc (DVD), optical storage disk, and/ any other computer data storage device. Removable storage drive 1314 reads from and/or writes to removable storage unit 1318 in a well-known manner.

Secondary memory 1310 may include other means, instrumentalities, or approaches for allowing computer programs and/or other instructions and/or data to be accessed by computer system 1300. Such means, instrumentalities or other approaches may include, for example, a removable storage unit 1322 and an interface 1320. Examples of the removable storage unit 1322 and the interface 1320 may include a program cartridge and cartridge interface (such as that found in video game devices), a removable memory chip (such as an EPROM or PROM) and associated socket, a memory stick and universal serial bus (USB) port, a memory card and associated memory card slot, and/or any other removable storage unit and associated interface.

Computer system 1300 may further include a communication or network interface 1324. Communication interface 1324 enables computer system 1300 to communicate and interact with any combination of remote devices, remote networks, remote entities, etc. (individually and collectively referenced by reference number 1328). For example, communication interface 1324 may allow computer system 1300 to communicate with remote devices 1328 over communications path 1326, which may be wired and/or wireless, and which may include any combination of local area networks (LANs), wide area networks (WANs), the Internet, etc. Control logic and/or data may be transmitted to and from computer system 1300 via communication path 1326.

In an embodiment, a tangible apparatus or article of manufacture comprising a tangible computer useable or readable medium having control logic (software) stored thereon is also referred to herein as a computer program product or program storage device. This includes, but is not limited to, computer system 1300, main memory 1308, secondary memory 1310, and removable storage units 1318 and 1322, as well as tangible articles of manufacture embodying any combination of the foregoing. Such control logic, when executed by one or more data processing devices (such as computer system 1300), causes such data processing devices to operate as described herein.

Based on the teachings contained in this disclosure, it will be apparent to persons skilled in the relevant art(s) how to make and use the invention using data processing devices, computer systems and/or computer architectures other than that shown in FIG. 13. In particular, embodiments may operate with software, hardware, and/or operating system implementations other than those described herein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A guide wire, comprising:
   at least one optical fiber configured to transmit a source beam of radiation, and
   a housing, comprising:
      a flexible substrate comprising a plurality of waveguides patterned thereon, wherein at least one of the plurality of waveguides is configured to transmit one or more beams of radiation away from the guide wire and at least one of the plurality of waveguides is configured to receive one or more beams of scattered radiation that have been reflected or scattered from a sample,
      a multiplexer configured to generate the one or more beams of radiation from the source beam of radiation,
      one or more ports through a wall of the housing,
      one or more optical elements configured to at least one of focus and steer at least one of the one or more beams of radiation, and
      one or more reflecting elements configured to direct the at least one of the one or more beams of radiation towards corresponding ports of the one or more ports.

2. The guide wire of claim 1, wherein the multiplexer is provided on the flexible substrate.

3. The guide wire of claim 1, wherein a distal end of the guide wire includes one or more cutting lips.

4. The guide wire of claim 1, wherein a distal end of the guide wire has a conical shape.

5. The guide wire of claim 1, wherein the multiplexer is a passive element.

6. The guide wire of claim 1, wherein the multiplexer is electrically driven.

7. The guide wire of claim 1, wherein at least one of the one or more optical elements includes a graded refractive index (GRIN) lens.

8. The guide wire of claim 1, wherein the plurality of waveguides are configured such that the at least one of the one or more beams of radiation are transmitted substantially parallel to an axis extending along a length of the guide wire and passing through a center of the guide wire.

9. The guide wire of claim 8, wherein the plurality of waveguides are spaced from each other by about 50 microns on the flexible substrate.

10. The guide wire of claim 8, wherein the at least one of the one or more beams of radiation is transmitted through an opening at a tip of a distal end of the guide wire.

11. The guide wire of claim 1, wherein the one or more reflecting elements are further configured such that the at least one of the one or more beams of radiation are transmitted at a non-zero angle with respect to an axis extending along a length of the guid wire and passing through a center of the guide wire and are transmitted away from the guide wire.

12. The guide wire of claim 11, wherein the non-zero angle is a 90 degree angle with respect to the axis and away from the guide wire.

13. The guide wire of claim 1, wherein the one or more reflecting elements include a spherical reflector.

14. The guide wire of claim 1, further comprising an actuator configured to rotate the guide wire about an axis extending along a length of the guide wire and passing through a center of the guide wire.

15. The guide wire of claim 14, further comprising a strain gauge configured to monitor strain induced upon the guide wire from the rotation.

\* \* \* \* \*